United States Patent
Hof

(10) Patent No.: US 8,215,958 B2
(45) Date of Patent: Jul. 10, 2012

(54) DENTAL IRRIGATOR

(75) Inventor: Refael Hof, Kfar Yona (IL)

(73) Assignee: Redent-Nova Ltd., Ra'anana (IL)

( * ) Notice: Subject to any disclaimer, the term of this patent is extended or adjusted under 35 U.S.C. 154(b) by 243 days.

(21) Appl. No.: 12/515,907

(22) PCT Filed: Nov. 21, 2007

(86) PCT No.: PCT/IL2007/001438
§ 371 (c)(1),
(2), (4) Date: May 21, 2009

(87) PCT Pub. No.: WO2008/062411
PCT Pub. Date: May 29, 2008

(65) Prior Publication Data
US 2010/0028830 A1 Feb. 4, 2010

(30) Foreign Application Priority Data
Nov. 23, 2006 (IL) .......................................... 179539

(51) Int. Cl.
*A61C 5/02* (2006.01)
*A61C 3/02* (2006.01)
(52) U.S. Cl. ........... 433/81; 433/102; 433/165; 433/224
(58) Field of Classification Search .................... 433/81, 433/102, 224, 80, 82, 84, 85, 87, 165, 166, 433/29–32, 88; 606/180, 107, 167–171; 604/118–121, 188, 264, 272–274; 366/305, 366/265; 29/896.1, 896.11
See application file for complete search history.

(56) References Cited

U.S. PATENT DOCUMENTS

| | | | |
|---|---|---|---|
| 4,608,017 A | 8/1986 | Sadohara | |
| 4,973,247 A | 11/1990 | Varnes et al. | |
| 5,310,341 A * | 5/1994 | Byer | 433/116 |
| 6,527,551 B2 | 3/2003 | Lanfranchi et al. | |

FOREIGN PATENT DOCUMENTS

| | | | |
|---|---|---|---|
| DE | 3433570 | * | 3/1983 |
| DE | 3433570 | | 3/1986 |
| EP | 0374276 B1 | | 6/1990 |
| EP | 0455452 B1 | | 11/1991 |
| FR | 2616652 A1 | | 12/1988 |

OTHER PUBLICATIONS

PCT/IL07/001438 Search Report Dated Mar. 10, 2008, 2 pages.

* cited by examiner

*Primary Examiner* — Todd Manahan
*Assistant Examiner* — Yogesh Patel
(74) *Attorney, Agent, or Firm* — Mark M Friedman

(57) ABSTRACT

The invention is a dental irrigator for delivering irrigant solution from an irrigation solution reservoir to the site of a dental procedure. The irrigator comprises: a hollow dental tool modified by the addition of one or more curved blades either formed directly on the neck of the tool or on a sleeve attached coaxially to the neck, one or more inlets associated with each of the curved blades, a housing that provides a watertight volume surrounding the inlets while allowing the tool to be freely moved with respect to the housing, and a supply hose, which conducts the irrigant solution at relatively low pressure from the reservoir to the housing. When the dental tool is attached to the distal end of a dental hand-piece and the hand-piece is activated causing the tool to move, irrigation solution enters the hollow interior of the neck of the tool and, as a result of the forces created by the motion of the curved blades, is delivered at relatively high pressure to the site.

9 Claims, 6 Drawing Sheets

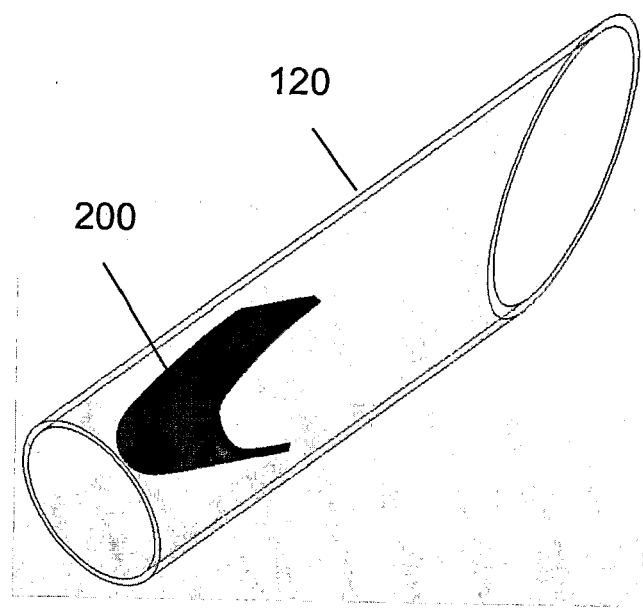
Fig. 9a
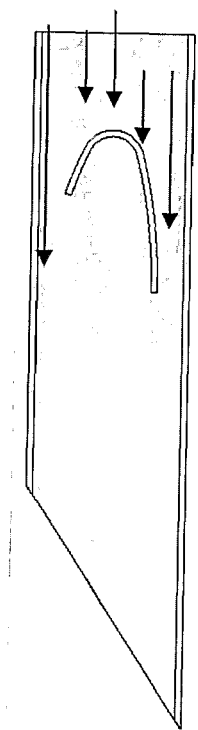 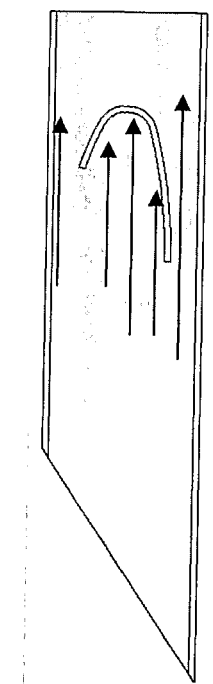
Fig. 9b                    Fig. 9c

DENTAL IRRIGATOR

This application is the National Stage of International Application No. PCT/IL2007/001438, filed Nov. 21, 2007, and claims benefit of Israel Application No. 179539, filed Nov. 23, 2006, both of which are incorporated by reference in their entirety.

FIELD OF THE INVENTION

The present invention relates to the field of dental irrigation devices. In particular, the present invention relates to an irrigation device which receives irrigant solution at relatively low pressure, and delivers it at relatively high pressure through the hollow interior of an endodontic file.

BACKGROUND OF THE INVENTION

During a root canal procedure, the dentist (or, endodontist) typically uses an endodontic file to remove tissue remnants to clean and shape the canal. While working the canal becomes clogged with dentin mud and debris, which interferes with the procedure. Since prior art root canal procedures are almost exclusively carried out using solid drills, the drill must be periodically withdrawn from the canal in order to introduce an antiseptic irrigant solution to flush out unwanted debris. The irrigant solution must to be supplied at relatively high pressure in order to effectively wash the debris out of the canal. Additionally, since the reason for performing a root canal procedure is frequently an infection of the pulp in the root canal and also because of the presence of large numbers of pathogens in the mouth, it is also necessary to thoroughly disinfect the canal, especially before obturation of the canal space and preferably during the course of the entire procedure.

U.S. Pat. No. 4,608,017 discloses a conventional endodontic irrigating instrument for irrigating the root canal of a tooth with an irrigating liquid. The instrument is a hand-piece similar to conventional dental hand-pieces. There is an aspiration needle at the distal end that is designed to insert into a clean or partially cleaned root canal. The instrument is connected directly to the office water and compressed air supplies. Water under pressure can flow through the instrument and out at the distal end in the form of an annular water jet surrounding the aspiration needle. The compressed air flows through a Venturi tube inside the instrument to create a partial vacuum that is used to draw the water and debris out of the canal through the aspiration needle. The flow rate and the pressure of the water and air are controlled manually by regulating valves. When it is desirable to perform irrigation with irrigating solutions such as peroxide solution instead of rinsing water, a container containing such solution may be provided and pressurized by introducing compressed air from a dental unit. The pressurized irrigating solution is then fed by a supply conduit to the head of the instrument.

The endodontic irrigating instrument disclosed in U.S. Pat. No. 4,608,017 is a dedicated device that is separate from the hand-piece used to shape and clean the canal with the endodontic file. In use the dentist must interrupt his work with the file, put it aside, pick up the irrigating instrument, operate it for a period of time, and then put it aside before continuing to work with the file.

U.S. Pat. No. 4,973,247 discloses a typical gas driven dental handpiece assembly. The assembly comprises a supply of compressed gas which operates a turbine for driving a high speed dental cutting or drilling tool. When working with a dental tool of this type a coolant and/or irrigant solution must be provided because of the frictional heat generated and to rinse away debris. The invention described in this patent is an addition to the hand-piece that provides an alternative to using the community water supply as a coolant or propellant fluid in order to provide a sterile working environment. The addition is a cartridge divided by a diaphragm containing coolant liquid on one side of the diaphragm. A mechanism is provided to allow the operator of the hand-piece to controllably divert the turbine drive gas to the empty part of the cartridge. The gas introduced into the cartridge exerts pressure on the diaphragm causing the coolant liquid to move under pressure out of the cartridge and toward the head of the dental tool where it is sprayed onto the work area from an opening located near the connection of the tool to the hand-piece. The sterility concerns are addressed by supplying a new cartridge for each patient.

U.S. Pat. No. 6,527,551 discloses a dental irrigation device aimed at overcoming the drawbacks of prior art systems that are cumbersome, complex and require permanent installations. The invention comprises an irrigant reservoir containing irrigant such as isotonic saline, water or medicaments, mountable on a dental delivery system. Pressurization means such as a standard source of air pressure for pressurizing irrigant is connectable to the reservoir. A handpiece is joined to the reservoir via a supply channel and comprises a standard dental handpiece interface for adapting with dental tools for dispensing irrigant, such as syringe irrigation tips.

The patents described above are typical of the approaches made in the prior art to providing irrigant solution to the site of the dental procedure. None of the prior art irrigant delivery systems of the prior art solve the basic problem of continuously supplying irrigant to the interior of a root canal during the cleaning and shaping phases of a root canal procedure. The problem is not limited to merely supplying the solution but also to supplying it at sufficient pressure to drive out the debris, to maintain the sterility of the surgical environment, and to supply it using a system that is convenient for the operator and as comfortable as possible for the patient.

It is an object of the present invention to provide a dental irrigation device that can be used with a suitable endodontic file to allow continuous flushing of the root canal while the file is inserted into the canal and engaged in cleaning and shaping it.

It is another object of the present invention to provide a dental irrigation device which receives fluid at relatively low pressure and delivers the fluid to the at relatively high pressure to the interior of the canal.

It is an additional object of the present invention to provide an irrigation device that can be retrofitted to existing dental hand pieces.

Additional objects and advantages of the present invention shall become apparent as the description proceeds.

SUMMARY OF THE INVENTION

The invention is a dental irrigator for delivering irrigant solution from an irrigation solution reservoir to the site of a dental procedure. The irrigator comprising:
 a) a hollow dental tool modified by the addition of one or more curved blades either formed directly on the neck of the tool or on a sleeve attached coaxially to the neck;
 b) one or more inlets associated with each of the curved blades;
 c) a housing that provides a watertight volume surrounding the inlets while allowing the tool to be freely moved with respect to the housing; and d) a supply hose, which conducts the irrigant solution at relatively low pressure from the reservoir to the housing.

When the dental tool is attached to the distal end of a dental hand-piece and the hand-piece is activated causing the tool to move, irrigation solution enters the hollow interior of the neck of the tool and, as a result of the forces created by the motion of the curved blades, is delivered at relatively high pressure to the site.

When activated the hand-piece may impart a rotational, a reciprocating linear, or a vibrational motion to the hollow dental tool.

When the hand-piece imparts a rotational motion to the hollow dental tool, the curved blades are preferably curved impeller blades. The curved impeller blades may extend either outwardly from the outer surface or inwardly into the interior of the neck or sleeve. In preferred embodiments the curvature of the curved impeller blades matches the shape of a cardioid curve.

In an embodiment wherein the hand-piece imparts a reciprocating linear motion to the hollow dental tool, the curved blade is located in the hollow interior of the neck or the sleeve.

In a preferred embodiment, the hollow dental tool of the dental irrigator of the invention is an endodontic file for use in a root canal procedure.

BRIEF DESCRIPTION OF THE DRAWINGS

FIG. 9a schematically shows a blade for an irrigator designed to be used with dental hand-piece that imparts a reciprocating linear motion to the hollow dental tool; and FIGS. 9b and 9c symbolically show respectively the movement resistance vector during the upstroke and downstroke of the blade of FIG. 9a through a solution.

DETAILED DESCRIPTION OF THE PREFERRED EMBODIMENTS

The invention is a dental irrigator, i.e. a delivery system that delivers irrigant solution at a relatively high pressure to the site of a dental procedure through the interior of a rotatable, hollow dental tool that is attached to the distal end of a dental hand-piece. The dental tool is modified by the addition of one or more curved blades and at least one inlet associated with each of the curved blades. The blades and inlets are either formed directly on the neck of the tool or on a sleeve that can be slid over or into the neck and attached to the neck or can serve as a collar to connect the neck of the tool to the dental hand-piece. The irrigant is delivered at low pressure, typically at or slightly over zero atmosphere gauge pressure to a housing that provides a watertight volume surrounding the inlets. The tool is attached to the distal end of a dental hand-piece. When the hand-piece is activated causing the tool to rotate, move reciprocally in a longitudinal direction or vibrate the irrigant is drawn into the hollow interior of the tool by means of the forces created by the motion of the blades.

The term, "irrigant solution" as used herein refers to any fluid solution for washing debris from a root canal, and/or for cooling a tooth and/or dental tool, and/or for disinfection of the canal.

The invention was developed to be used for root canal treatment in conjunction with a new type of endodontic file invented by the inventor of the present invention. The endodontic file was described previously in published international patent application WO2005/070320, by the same applicant, the description of which, including publications referenced therein, is incorporated herein by reference. The use of this drill to perform root canal procedures has been chosen in order to illustrate the principles of the invention; however, as the description herein develops it will become apparent to skilled persons that the present invention can be adapted to be used for many other applications and with many different types of hollow tools.

Figure 1:
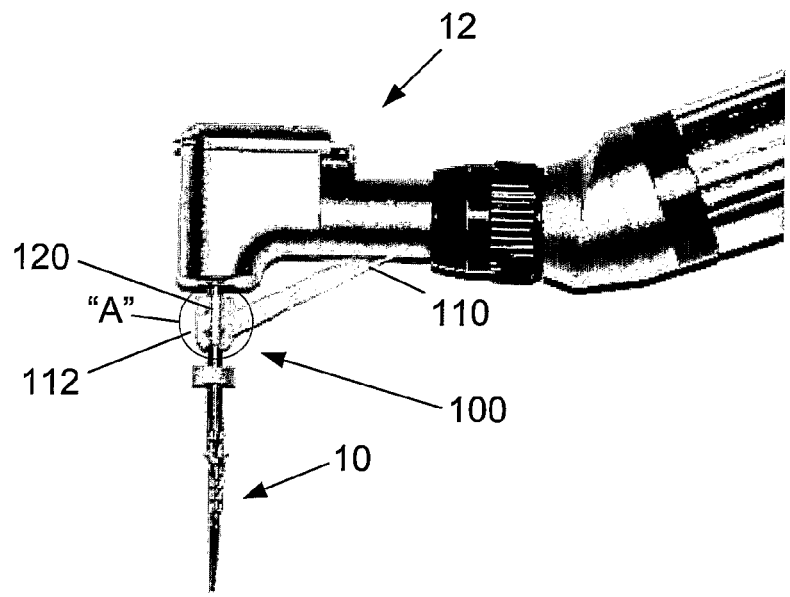
FIG. 1 shows an overall view of the invention.

FIG. 1 shows an overall view of the invention. In FIG. 1 can be seen rotatable endodontic file (10) joined at the proximal end of its neck (120) to a conventional dental hand piece (12). File (10), shown in FIG. 1 and in an enlarged view in FIGS. 2a and 2b in perspective and side views respectively. Dental file (10) is made of a shaped memory material, preferably nickel titanium alloy (Nitinol). In the figures is shown an embodiment of the tool in its expanded configuration, which has the cylindrical shape that was imposed upon it during manufacture. The walls of the neck (120) are solid and are gripped by either the dental hand piece (12) or can be attached to a handle for manual use. The main part of the body of dental file (10) is an open, lattice-like structure made up of longitudinal elements (6) that run the length of the instrument from neck (120) to tip (4) and short circumferential elements (2) that connect adjacent longitudinal elements (6).

The structure of the file allows it to be compressed reducing its diameter as it is inserted into a root canal. As the file (10) rotates, material is scraped from the wall of the root canal and passes through the openings in the lattice structure of the body of dental file (10) into the hollow interior from which it can easily be removed without stopping rotation of the instrument or withdrawing it from the root canal by use of suction or by causing a stream of clean irrigant solution to flow into the file. The shaped memory property causes the file to continuously try to expand from its compressed to its expanded configuration. Therefore, as material is scraped from the wall, the file expands keeping constantly in contact with the canal wall and allowing removal of material from the wall without changing the inherent shape of the canal.

Figure 2A:
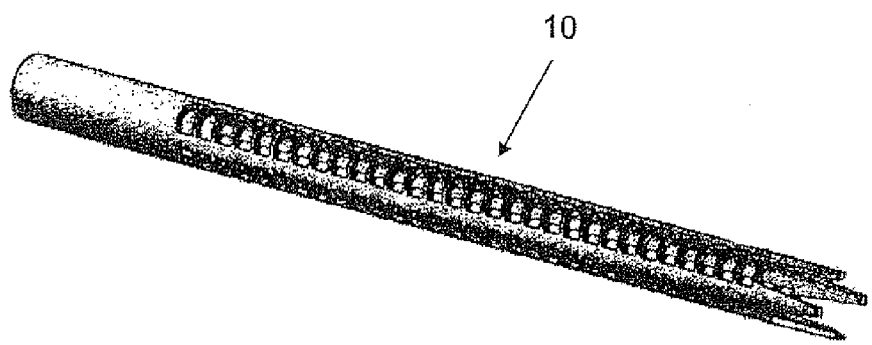
FIGS. 2a and 2b illustrate an endodontic file having an open lattice-like structure.
Figure 2B:
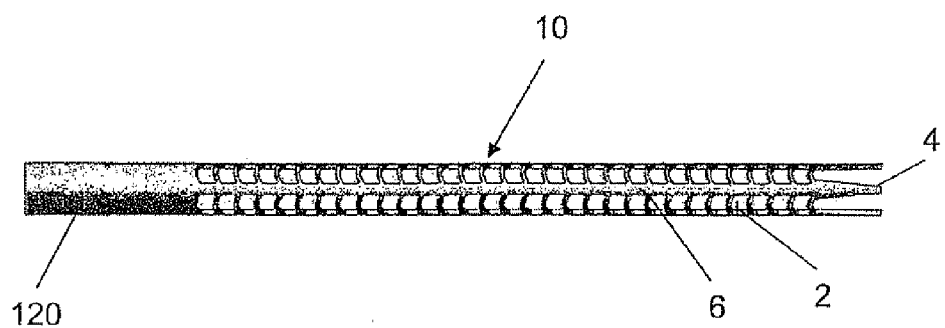

The novel design of the drill shown in FIGS. 2a and 2b provides the possibility for fluids, such as antiseptic or saline solution, to continuously flow into and out of the root canal, either through the center of the instrument or between the outer surface of the instrument and the canal wall, while the instrument is working, thus saving valuable time and improving the debridement and disinfection procedures. The constant flow increases the efficiency of filing and prevents clogging of the canal with dentin-mud and debris.

Figure 3:
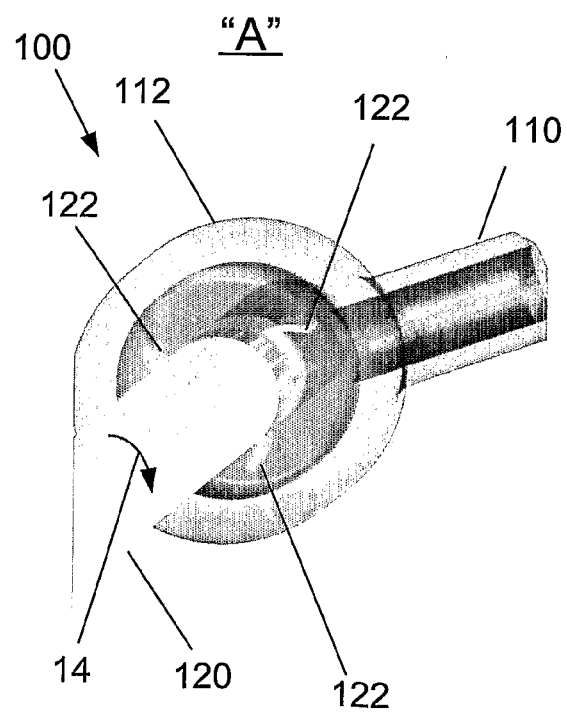
FIG. 3 illustrates an enlarged view of a portion of the irrigation device of the present invention.

A preferred embodiment of the irrigation system of the present invention will now be described with reference to FIG. 1 and FIG. 3, which is an enlarged bottom perspective view of area "A" in FIG. 1. The system of the invention is generally described by the numeral (100). The main feature of irrigation system 100 is the three curved impeller blades (122) that have been created on the neck (120) of the drill (10). The blades (122) are spaced equidistantly along the circumference of neck (120) and extend curvedly outward from neck (120) in the direction of rotation of dental file (10), which is indicated by arrow (14) (see FIG. 3). Irrigation device (100) further comprises a housing (112) surrounding impeller blades (122), as described herein below.

Although three blades (122) are shown in the figures, it is understood that fewer or more than three blades (122) may be provided, depending on the diameter of neck (120), among other parameters.

Figure 4:
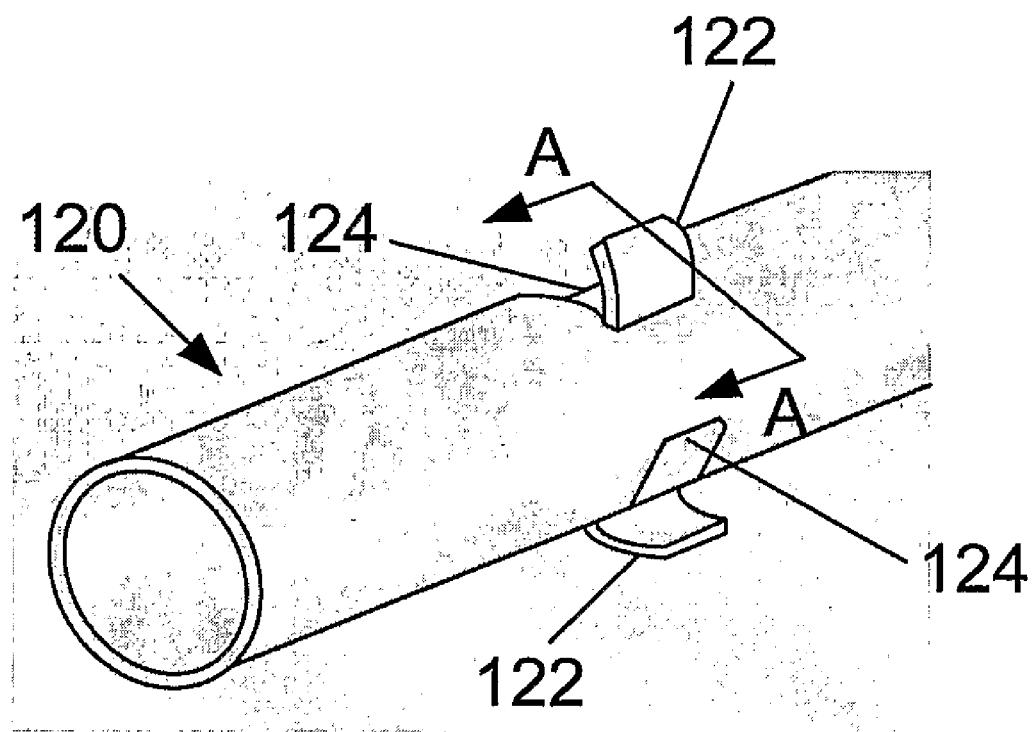
FIG. 4 shows an enlarged view of the neck of the file.
Figure 5:
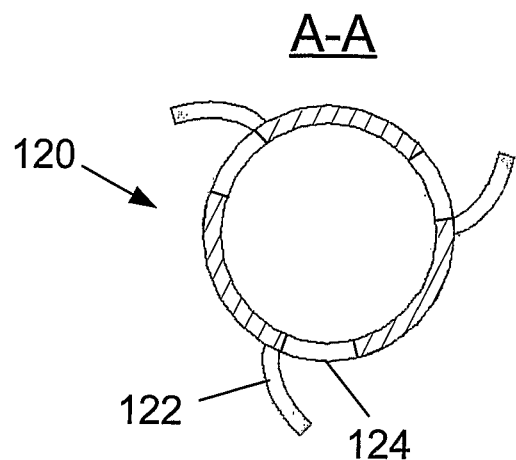
FIG. 5 shows a cross-sectional view taken in pane A-A of FIG. 4.

FIG. 4 shows an enlarged view of the neck (120) of the file. FIG. 5 shows a cross-sectional view taken in plane A-A of FIG. 4. An inlet (124) is created through the wall of the neck (120) at the inside of the curvature opposite each impeller blade (122). If the area of neck (120) containing the impeller blades (122) and associated inlets (124) is surrounded by a liquid, then when the file is rotated rapidly by the hand-piece, a low pressure area will be created on the inner side of the curved impeller blades, causing the liquid to enter the interior of the drill through inlets (124). The liquid that enters through inlets (124) will be directed towards the bottom of the file, i.e. into the root canal, at a high velocity and much higher pressure relative to the pressure of the liquid that is supplied at the outside of the neck (120).

Figure 6:
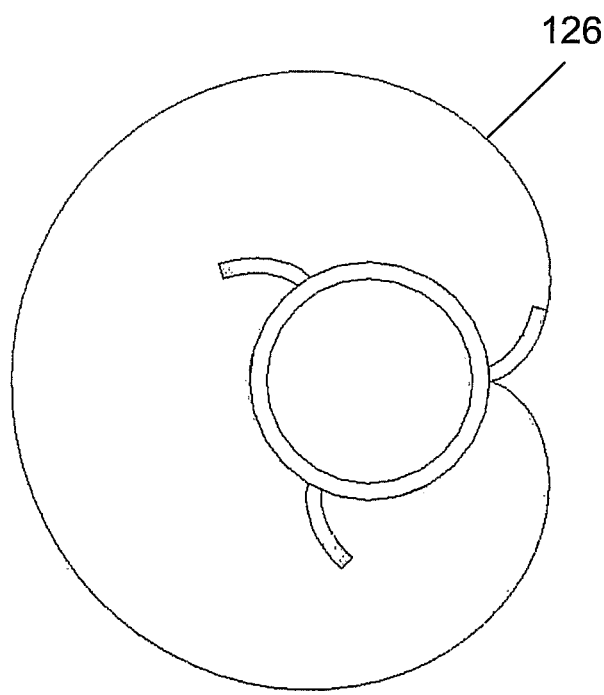
FIG. 6 shows the cardioid shape of the impeller blade.

The design of the impeller blades is not a part of the present invention. Skilled persons will be able to use well known methods of fluid flow to arrive at the optimal design while taking into account such factors as the inner and outer diameters of the neck (120), flow rate, supply pressure, desired delivery pressure, viscosity of the liquid, etc. The inventor has determined that excellent results can be obtained by making the curvature of the impeller blade (122) match the shape of a cardioid curve (126) as shown in FIG. 6.

Figure 7:
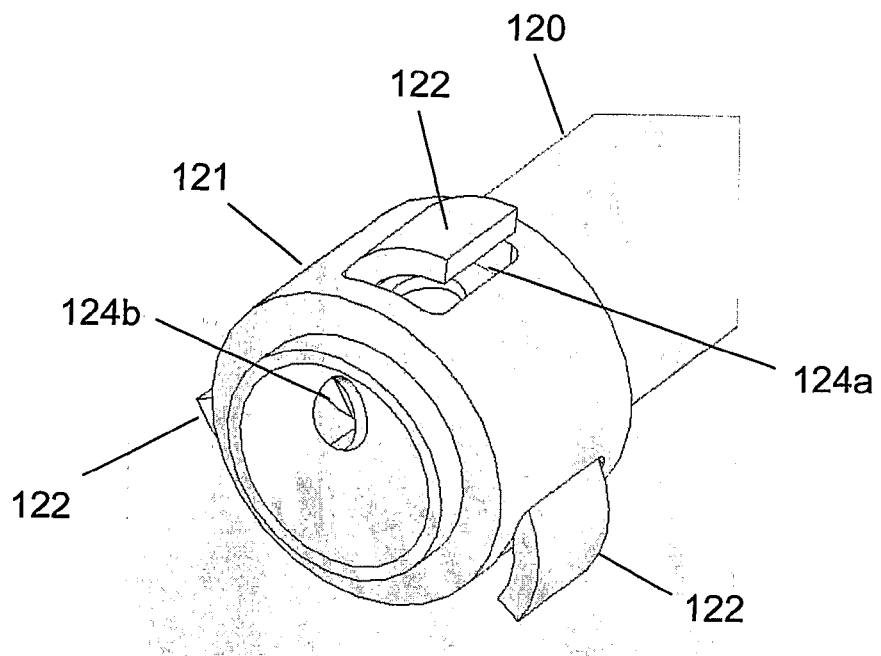
FIG. 7 an embodiment of the present invention in which the impeller blades are located on a sleeve attached to the neck of the file.

In the embodiment of the invention shown in FIG. 3 to FIG. 6, impeller blades (122) are integrally formed out of neck (120), i.e. blades (122) and neck (120) are manufactured as a single piece. In an alternative embodiment, as shown in FIG. 7, the impeller blades (122) are formed on a separate sleeve (121). Sleeve (121) is positioned around neck (120) such that inlets (124a) are aligned with holes (124b) in neck (120). Sleeve (121) is fixed in place by conventional means such as a set screw, or alternatively, sleeve (121) may be threadingly engaged with neck (120). In FIG. 7, sleeve (121) is shown shortened in order to show its orientation with respect to neck (120), but in reality, either the sleeve or neck must extend longitudinally enough to allow it to be attached to the hand-piece.

Figure 8:
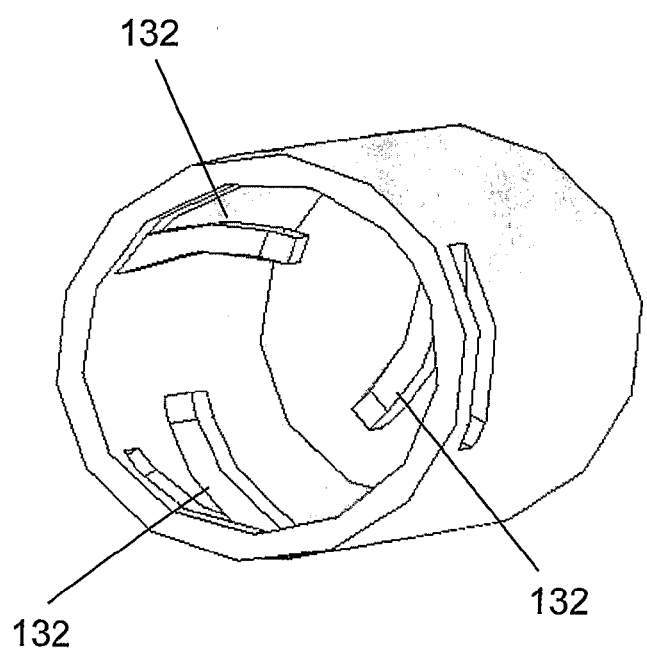
FIG. 8 shows another design of the impeller blades.

In yet another embodiment of the invention shown in FIG. 8, the impeller blades (132) extend curvedly inwards into the hollow internal space of neck (110). In this embodiment the impeller blades can be formed on a bushing that is inserted into the hollow neck (120).

In order to supply the irrigant to the impellers, a watertight housing (112) is provided as part of the irrigator. Many different possible embodiments of housing (112) are possible. In all cases, the dental file (10) must be allowed to freely rotate while the housing (112) itself is constrained in some manner from rotating relative to the hand-piece. To allow rotation of file (10) while preventing irrigant solution from leaking out of housing (112), a seal such as an o-ring is situated at the upper and lower ends of housing (112) and a suitable lubricant, e.g. silicon grease, is applied to the o-ring to reduce friction as the tool rotates. The housing can be permanently attached to the distal end of the hand-piece (12), it can be attachable to and detachable from the distal tip of the hand piece (12), or it can take the form of a capsule that is either permanently attached to or slid onto the file. In the latter case an arrangement is provided to prevent rotation of the capsule relative to the hand-piece.

A connector is provided on housing (112) in order to connect a supply hose (110), which is provided to conduct the irrigant from the reservoir (not shown in any of the figures) to the interior of the housing. A section of supply hose (110) may pass through the hand-piece (12) as shown in FIG. 1 or supply hose (110) may directly join the reservoir to housing (112). In preferred embodiments a valve of some sort is provided to allow the flow of irrigant to the housing, i.e. into the root canal, to be controlled by the dentist. As is customary, the valve is conveniently activated by means of a foot pedal.

In the embodiment described herein above, the dental tool is attached to a hand-piece that imparts rotary motion to the tool. The invention can also be used with hand-pieces that impart reciprocating linear motion to the tool, normally in the direction of the longitudinal axis of the tool, or vibrational motion in any direction.

In FIG. 9a is schematically shown a blade 200 inserted into the neck 120 of a hollow dental tool, for example the endodontic file described herein above. Not shown in FIG. 9a is the inlet into the interior of the neck and the housing that surrounds it. The tool is connected to a dental hand-piece that imparts a reciprocating linear motion to the tool, moving the tool and attached blade up and down relative to the housing. The blade is designed so that on the down stroke most of the liquid that is inside the "cup" of the blade is swept downward, as shown in FIG. 9c. On the upstroke the blade cuts upward through the liquid, pushing it against the walls of the housing and forcing it downward into the neck around the sides of the blade. The arrows that are shown in FIGS. 9b and 9c symbolically represent the movement resistance vector as the blade moves up and down through the solution inside the neck of the dental tool.

In the preferred embodiment, the irrigant solution reservoir is a plastic bag similar to an infusion bag. The reservoir can be laid on the table that is attached to the dentists chair and used to lay out the instruments used during the procedure. As long as the table is essentially at least on the same level as the housing (112) the action of the impellers will be sufficient to draw irrigant from the bag at a rate sufficient to remove the debris from the root canal. The irrigator (100) of the invention therefore avoids the problem of gravity fed irrigators of having to hang the supply container high above the patient in order to provide enough elevation to allow irrigant solution to flow to the treatment area under the influence of gravity and to arrive at a high enough pressure to be effective.

Any other type of reservoir known in the art or devised by skilled persons that can deliver the irrigant to the housing (112) at a gauge pressure of essentially zero may be used with the irrigation device of the invention. For example, the irrigant may be supplied in a plastic bag, which is placed in a container comprising a moveable surface that, with the aid of springs presses against the bag forcing the liquid inside into the supply hose (110). Another more expensive alternative is for the reservoir to be a syringe and a syringe pump is used to force irrigant solution out of the syringe. The pump may be arranged to push a small amount of irrigant solution out of the syringe at a constant rate, or at preset time intervals, or the pump may be manually actuated.

Typically the endodontic file (10) is discarded after each procedure and similarly it is preferred that all of the components of the irrigation system of the invention are disposable also although it is also possible to manufacture all or part of the system from sterilizible materials allowing them to be reused.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

The invention claimed is:

1. A dental irrigator for delivering irrigation solution from an irrigation solution reservoir to the site of a dental procedure, said irrigator comprising:
   a) a hollow dental tool comprising a neck;
   b) one or more inlets created through the wall of said neck;
   c) a housing adapted to provide a volume of irrigation solution around said inlets while allowing said tool to be freely movable with respect to said housing;
   d) a supply hose, which conducts the irrigation solution at relatively low pressure from the reservoir to said housing; and
   e) a curved blade located in the hollow interior of one of (i) the neck of the hollow dental tool and (ii) a sleeve attached coaxially to said neck, the curved blade shaped such that when the hollow dental tool is attached to a dental hand-piece and said hand-piece is activated causing the hollow dental tool to move in a reciprocating linear motion with respect to the housing, said irrigation solution flows into the hollow interior of said neck of said tool and as a result of forces created by the motion of the curved blade is delivered at relatively high pressure to the site, and said curved blade extends curvedly inwards into a hollow internal space of said neck.

2. A dental irrigator according to claim 1, wherein the blade has a cupped shape.

3. A dental irrigator according to claim 2, wherein the blade is configured such that on a down stroke of the reciprocating linear motion of the hollow dental tool the blade pushes downward against liquid inside the cup-shaped blade.

4. A dental irrigator according to claim 1, wherein the housing of the hollow dental tool is configured to attach to a distal end of a dental hand-piece.

5. A dental irrigator according to claim 1, wherein the blade has a downwardly cupped shape.

6. A dental irrigator according to claim 5, wherein the hollow dental tool has an open lattice-like structure.

7. A dental irrigator according to claim 1, wherein the hollow dental tool is an endodontic file.

8. A dental irrigator according to claim 1, wherein the site of the dental procedure is a root canal.

9. The dental irrigator of claim 1, wherein the irrigation solution reservoir is a flexible plastic bag such that the irrigation solution reservoir is capable of being laid on a flat surface of a table.

* * * * *

UNITED STATES PATENT AND TRADEMARK OFFICE
CERTIFICATE OF CORRECTION

Page 1 of 1

PATENT NO. : 8,215,958 B2
APPLICATION NO. : 12/515907
DATED : July 10, 2012
INVENTOR(S) : Refael Hof It is certified that error appears in the above-identified patent and that said Letters Patent is hereby corrected as shown below:

Front page

Column 7

Claim 1 line 12 should be corrected as follows:
Change:
-- a housing adapted to provide a volume of irrigation --
to
"a watertight housing adapted to provide a volume of irrigation"

Column 7

Claim 1 line 14 should be corrected as follows:
Change:
-- freely movable with respect to said housing; --
to
"freely moved with respect to said housing;"

Signed and Sealed this
Eleventh Day of September, 2012

David J. Kappos
*Director of the United States Patent and Trademark Office*